(12) United States Patent
Alhusain

(10) Patent No.: US 8,997,551 B2
(45) Date of Patent: Apr. 7, 2015

(54) APPARATUS FOR DETERMINING COEFFICIENTS OF FRICTION

(75) Inventor: Museb Saleh Alhusain, Bayan (KW)

(73) Assignee: Kuwait University, Safat (KW)

( * ) Notice: Subject to any disclaimer, the term of this patent is extended or adjusted under 35 U.S.C. 154(b) by 358 days.

(21) Appl. No.: 13/604,505

(22) Filed: Sep. 5, 2012

(65) Prior Publication Data

US 2014/0060149 A1    Mar. 6, 2014

(51) Int. Cl.
*G01N 3/56* (2006.01)
*G01N 19/02* (2006.01)

(52) U.S. Cl.
CPC ...................... *G01N 19/02* (2013.01)

(58) Field of Classification Search
CPC . G01N 19/02; G01N 19/04; G01N 2033/008; G01N 33/42; A63B 2220/16; A63B 2220/18; A63B 2220/20; A63B 2220/30; A63B 2071/025; D06F 77/00; A63D 5/00
USPC .............................................................. 73/9
See application file for complete search history.

(56) References Cited

U.S. PATENT DOCUMENTS

| | | | |
|---|---|---|---|
| 2,913,896 A | 11/1959 | Barron | |
| 3,020,744 A | 2/1962 | Long | |
| 3,098,377 A * | 7/1963 | Beauchamp | 73/9 |
| 5,107,448 A | 4/1992 | Nash | |
| 5,245,856 A | 9/1993 | Pazzaglia et al. | |
| 5,538,122 A * | 7/1996 | Siemens | 194/207 |
| 7,299,571 B2 * | 11/2007 | Krasner et al. | 38/74 |
| 7,600,411 B2 | 10/2009 | Bailey | |
| 8,249,714 B1 * | 8/2012 | Hartman et al. | 607/48 |
| 2006/0130556 A1 | 6/2006 | Olde Weghuis et al. | |
| 2011/0237399 A1 * | 9/2011 | Toback et al. | 482/8 |

* cited by examiner

*Primary Examiner* — Daniel S Larkin
*Assistant Examiner* — Jamar Ray
(74) *Attorney, Agent, or Firm* — Richard C Litman

(57) ABSTRACT

The apparatus for determining coefficients of friction collects data required for determining static and dynamic coefficients of friction between various materials. The apparatus includes a ramp with adjustable slope and a plurality of test masses for placement on the ramp. Upslope lights and sensors, downslope lights and sensors, and a digital angle meter are installed on the ramp. The apparatus has a timing device having a display to show the elapsed time between a test mass passing the upslope sensor and the downslope sensor. The operator can determine the static coefficient of fraction from the tangent of the angle displayed on the digital angle meter when a test mass first begins to slide, and can compute the kinetic coefficient of friction from the angle displayed on the digital angle meter and the elapsed time shown on the timing device.

8 Claims, 5 Drawing Sheets

APPARATUS FOR DETERMINING COEFFICIENTS OF FRICTION

BACKGROUND OF THE INVENTION

1. Field of the Invention

The present invention relates generally to devices for determining the physical properties of materials, and particularly to an apparatus for determining coefficients of friction of various materials as they travel along a surface. The surface material may be interchanged for testing the various materials as they travel over different surfaces.

2. Description of the Related Art

The precise determination of the physical properties of various materials is useful in many fields in addition to the purely theoretical or academic world. An example of such is found in the determination of the static and dynamic (sliding) coefficients of friction between paved surfaces and vehicle tires traveling over those surfaces. Different surfaces, e.g., asphalt or concrete, exhibit different static and dynamic coefficients of friction between those surfaces and a given rubber tire bearing upon the surfaces. Moreover, in the past it was believed that tires having a tread pattern (grooves, etc.) provided greater static or rolling adhesion to the underlying surface than did "slick" tires, i.e., tires having an unbroken rubber surface devoid of grooves and/or other discontinuities. This has been shown to be erroneous. Tires having a smooth, unbroken surface are recognized as providing a higher static coefficient of friction, i.e., greater adhesion, than tires having a tread pattern, at least on dry surfaces. The only means of precisely establishing these factors is through precise tests.

The precise determination of dynamic or sliding coefficients of friction between different materials is also useful in the reduction of internal resistance in various mechanical devices, such as internal combustion engines, transmissions, and differentials. This particular field has assumed great importance, as even very small improvements in efficiency result in significant reductions in wasted energy and significant improvements in fuel economy when a large fleet of vehicles (automobiles, aircraft, ships, etc.) is considered.

None of the above inventions and patents, taken either singly or in combination, is seen to describe the instant invention as claimed. Thus, an apparatus for determining coefficients of friction solving the aforementioned problems is desired.

SUMMARY OF THE INVENTION

The apparatus for determining coefficients of friction includes a flat, level base having an adjustable slope ramp attached thereto at one end. The ramp preferably includes a plurality of different surface overlays of material that may be interchanged. A plurality of different masses may be placed upon the elevated end of the sloped ramp to determine the coefficient of friction between the specific mass and the specific overlay upon the ramp. Maximum static (stationary) coefficient of friction is determined at the ramp inclination immediately before movement of the mass down the slope of the ramp. The dynamic (sliding) coefficient of friction is determined by considering the slope of the ramp and the velocity of the mass as it slides down the ramp.

The apparatus includes upslope and downslope sensors and corresponding upslope and downslope lights aimed at the sensors. The lights may be visible or infrared, and used with corresponding visible light or infrared light receiving sensors. The sensors transmit a signal to a timer having an elapsed timing device when the upslope and downslope lights are broken by the mass as it slides through the light beams as it travels down the sloped ramp. Alternatively, the light and sensor may be located together, so that the sensor detects changes in reflected light as the mass passes through the beam of light. The timer determines the travel time for the mass between the two lights and displays the elapsed time. A digital angle meter is also provided, and displays the angle of the ramp. The net result is that the apparatus provides all of the data for the operator to determine both the static and dynamic coefficients of friction nearly instantly for any given test.

Various embodiments are disclosed, with the embodiments differing primarily by the means used to adjust the slope of the ramp. In one embodiment, a winch is installed at the lower end of the ramp and a cable extends across a boom to the opposite elevating end of the ramp. Another embodiment provides a jackscrew in place of the winch. In yet another embodiment, the jackscrew is installed beneath the elevating end of the ramp, opposite its attachment to the base.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
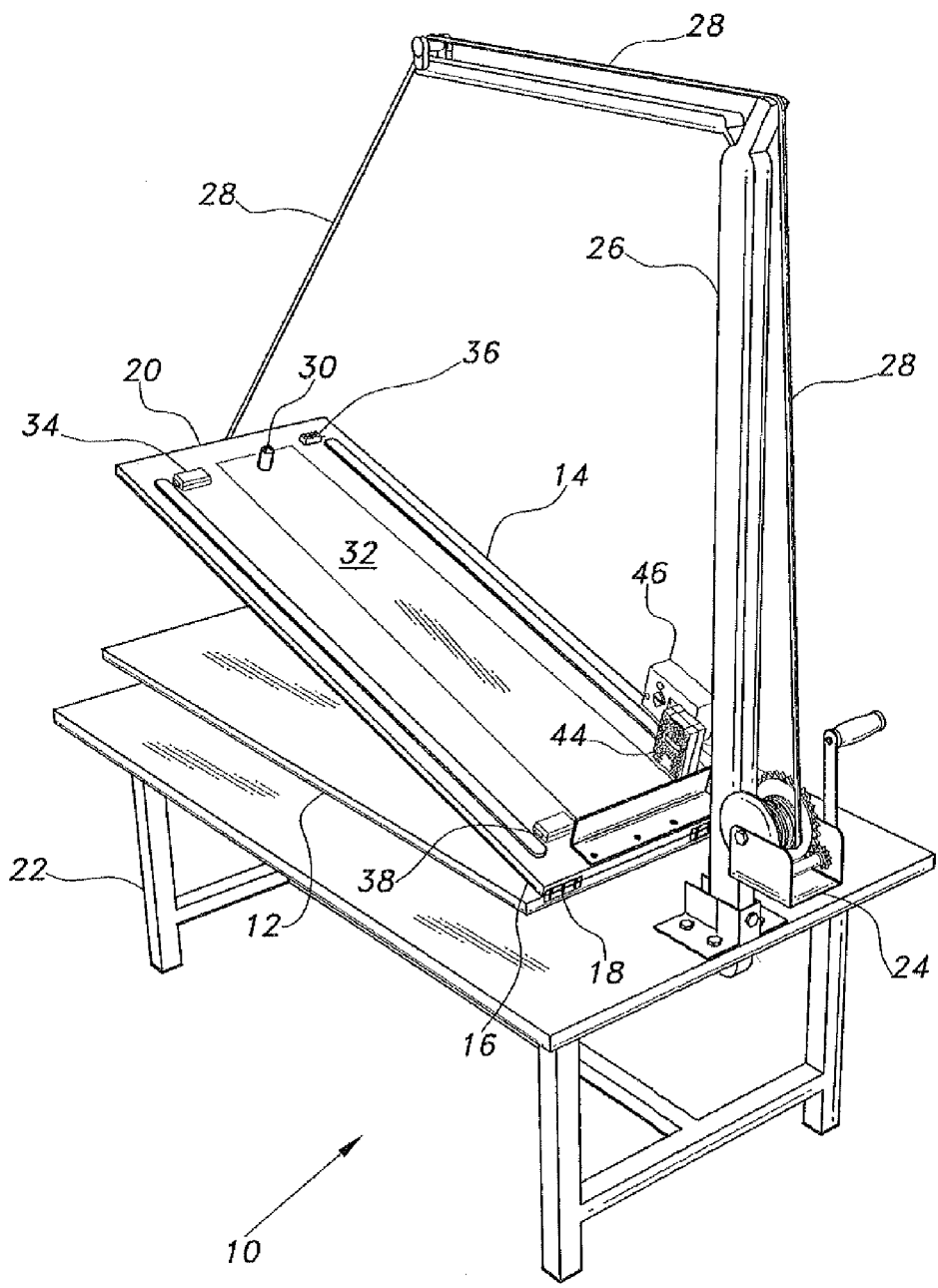
FIG. 1 is a perspective view of a first embodiment of an apparatus for determining coefficients of friction according to the present invention, illustrating its general features and operation.

The apparatus for determining coefficients of friction is capable of measuring or determining the data required to enable an operator or other party to calculate both the static and dynamic coefficients of friction between different surfaces. FIG. 1 of the drawings provides a general overview of a first embodiment of the apparatus incorporating a manually actuated winch for the adjustment of the slope of the ramp. The apparatus 10 includes a flat, planar base 12 having an adjustable slope ramp 14 disposed thereabove. The ramp 14 has a base attachment end 16 attached to the base 12 by one or more hinges 18, and an opposite elevating end 20. The elevating end 20 of the ramp 14 is vertically adjustable, allowing the slope of the ramp 14 to be adjusted. The apparatus 10 may be installed or supported upon a table 22, workbench, counter, or other elevated surface for convenience.

Figure 2:
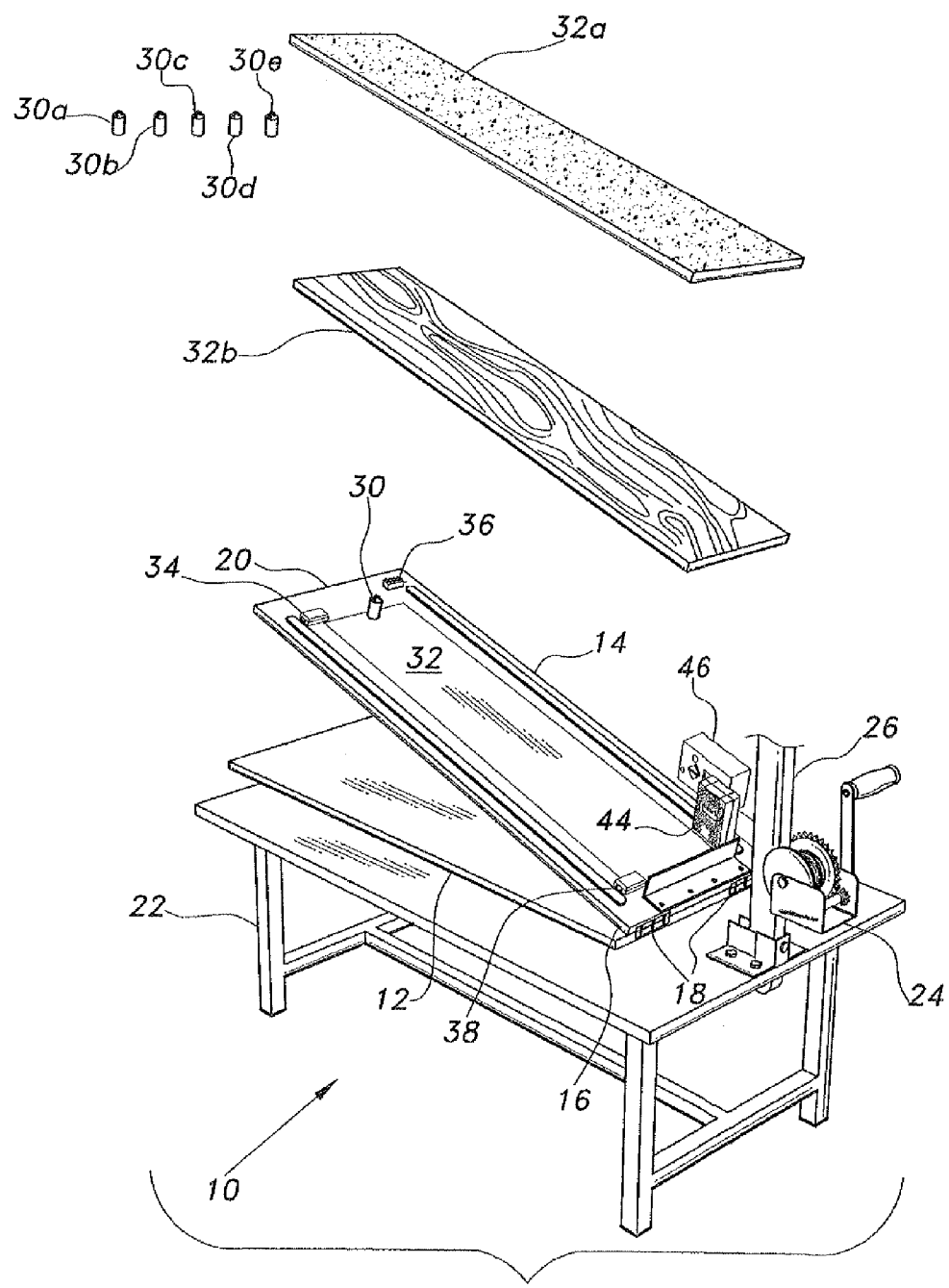
FIG. 2 is an exploded partial perspective view of the apparatus of FIG. 1, illustrating a plurality of replaceable ramps having different surfaces and a plurality of masses having different coefficients of friction furnished as a kit with the apparatus.
Figure 3:
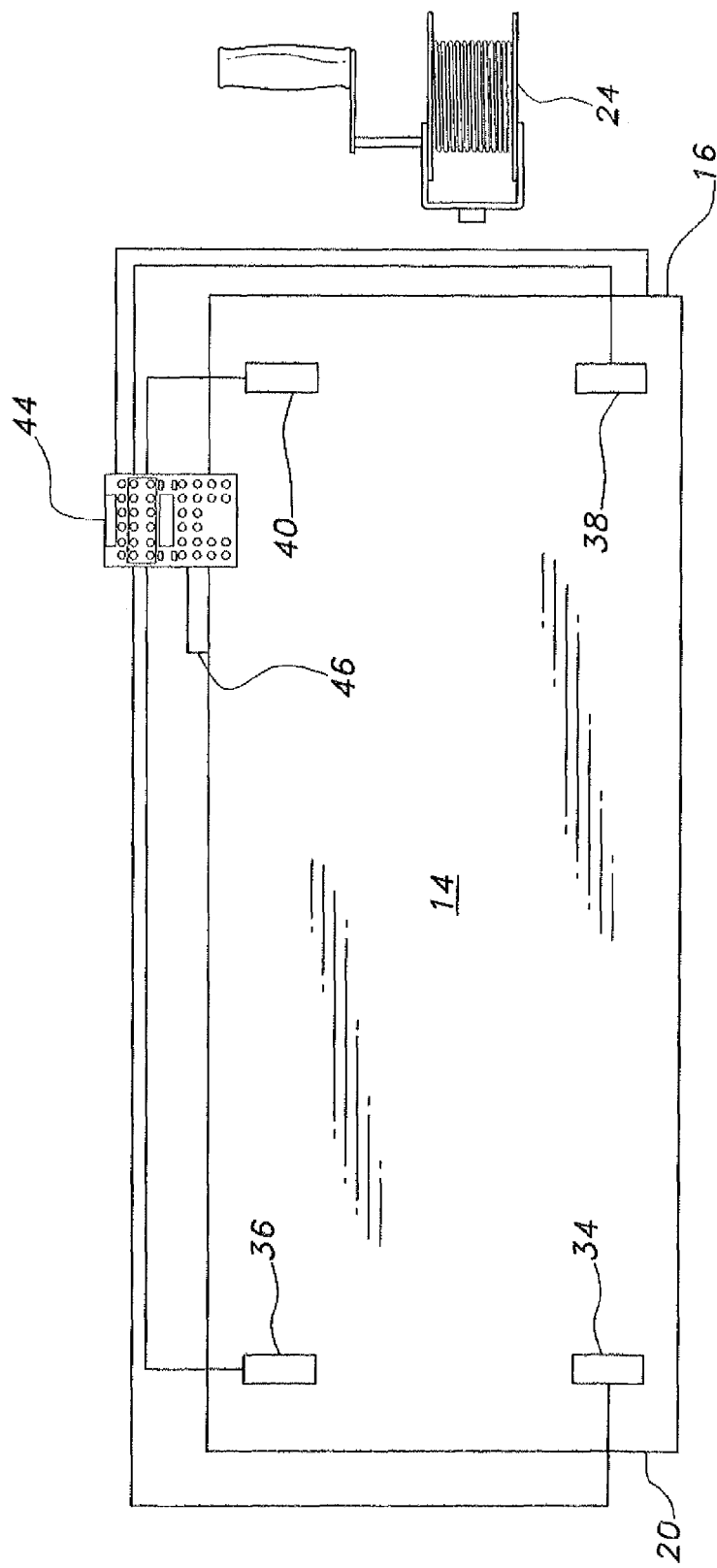
FIG. 3 is a diagrammatic top plan view of the apparatus of FIG. 1, illustrating the electronic sensing and recording components and other features.

A variety of different ramp elevation mechanisms or devices may be provided to continuously adjust the slope of the ramp 14. In the example of FIGS. 1 through 3, a manually actuated ratchet winch 24 is used to adjust the slope of the ramp 14. The winch 24 is affixed to the base of a column 26 (broken away in FIG. 2 in order to clearly illustrate other features), which may be attached to the underlying top of the table 22 or to an extension of the base 12. A lift cable 28 extends from the winch 24, over the top of the column 26 and along an arm or boom extending from the top of the column 26, and down to the elevating end 20 of the ramp 14. Winding the cable 28 upon the winch 24 draws the distal end of the cable 28 upward over the column 26 and its arm, thereby raising the elevating end 20 of the ramp 14. Release of the ratchet mechanism of the winch 24 allows the cable 28 to extend, thereby lowering the elevating end 20 of the ramp 14.

FIG. 2 illustrates further features of the apparatus 10. The apparatus is used by placing a cylindrical mass, e.g., the mass 30 shown at the elevating end 20 of the ramp 14 in FIGS. 1, 2, 4, and 5, upon the elevating end 20 of the ramp 14 and tilting the ramp 14 until the mass 30 slides down the friction surface 32 of the ramp. In this manner, the maximum static coefficient of friction between the mass 30 and the friction surface 32 may be determined based upon the maximum slope angle of the ramp 14 immediately before the mass 30 begins to move. The data for the determination of the dynamic coefficient of friction is determined by measuring the velocity of the mass 30 as it travels down the sloped surface 32 of the ramp 14. Clearly, different friction surfaces and masses will develop different coefficients of friction therebetween. Accordingly, a plurality of test masses 30a, 30b, 30c, 30d, 30e, etc. is preferably provided with the apparatus 10, the various test masses 30 through 30e each being of different material and having different surface coefficients of friction from one another.

A corresponding plurality of different friction test surfaces 32a, 32b, etc. is also provided. For example, the test surface 32 shown atop the ramp 14 is a smooth surface of metal, plastic, or other smooth material. The uppermost test surface 32a of FIG. 2 may have a roughened texture, e.g., asphalt paving, concrete, etc., while the intermediate test surface 32b may comprise a sheet of wood, etc. All of these various friction test surfaces 32, 32a, 32b, etc. may be interchangeably installed atop the ramp 14, depending upon the specific materials being tested.

FIG. 3 of the drawings is a diagrammatic top plan view illustrating the general layout of the electronic components of the apparatus 10 for determining coefficients of friction, most of these components also being shown in FIGS. 1, 2, 4, and 5. In order for the apparatus 10 to be used to determine the dynamic coefficient of friction of different materials, the velocity of the test mass, e.g., mass 30, etc., must be measured as the mass travels over the test surface of the inclined ramp 14. Accordingly, a starting light 34 (which may be an LED, either of visible light or an infrared LED) and corresponding starting light sensor 36 (i.e., a phototransistor or photocell) are installed adjacent the elevating end 20 of the ramp 14. The starting light 34 is installed at one edge of the ramp 14, and the starting light sensor 36 is installed at the laterally opposite edge of the ramp. A corresponding ending light 38 and ending light sensor 40 (the sensor 40 is shown only in FIG. 3) are installed adjacent the base attachment end 16 of the ramp 14, again adjacent the laterally opposed edges of the ramp. These lights 34, 38 and sensors 36, 40 may transmit and receive visible light, or may be infrared units. The lights and sensors 34 through 40 operate using the principle of starting an elapsed timer when the beam of light between the starting light and sensor 34 and 36 is broken, and stopping the elapsed timer when the beam of light between the ending light and sensor 38 and 40 is broken. Alternatively, the starting light and starting sensor and corresponding ending light and ending sensor may be included in single units, so that the sensors registering changes in reflected light as the test mass passes through the light emitted by the starting and ending lights.

A timing device 46 is also provided. The various lights and sensors 34 through 40 communicating electronically with the timing device 46, generally as shown in the diagrammatic view of FIG. 3. The timing device 46 has a display that displays the elapsed time for the mass 30 to slide down the ramp 13 between the starting sensor 36 and the ending sensor 40. Any suitable device that has a processor for subtracting the time of the start signal from the time of the finish signal and that can display the elapsed time may be used as a timing device 46. In a prototype of the apparatus 10, a Lego Mindstorms RCX robotic controller, which has a programmable microcontroller and comes with a pair of sensors, was used as an elapsed timer for measuring the time interval as determined by the lights and timers. An electronic digital angle meter 44, which has an electronic display to show the slope angle of the ramp, is also provided on the adjustable ramp 14. An example of such a digital angle meter is the Slope View TLL-90, which may be installed upon the ramp 14 as a standalone unit to measure the slope of the ramp. Thus, the timing device 46 registers the time at which the starting light beam is broken as the test mass first begins to move, receives a signal from the ending light sensor 40 when the test mass travels through the beam emitted by the ending light 38, and displays the elapsed time. This allows the operator of the apparatus to determine the velocity of the test mass, as the length of the test surface (or distance between the starting sensor 36 and ending sensor 40) is known. The final factor is the angle of the slope of the test surface (established by the ramp 14 and measured by the digital angle meter 44). These factors are used to determine the dynamic coefficient of friction between the given test mass and test surface.

Figure 4:
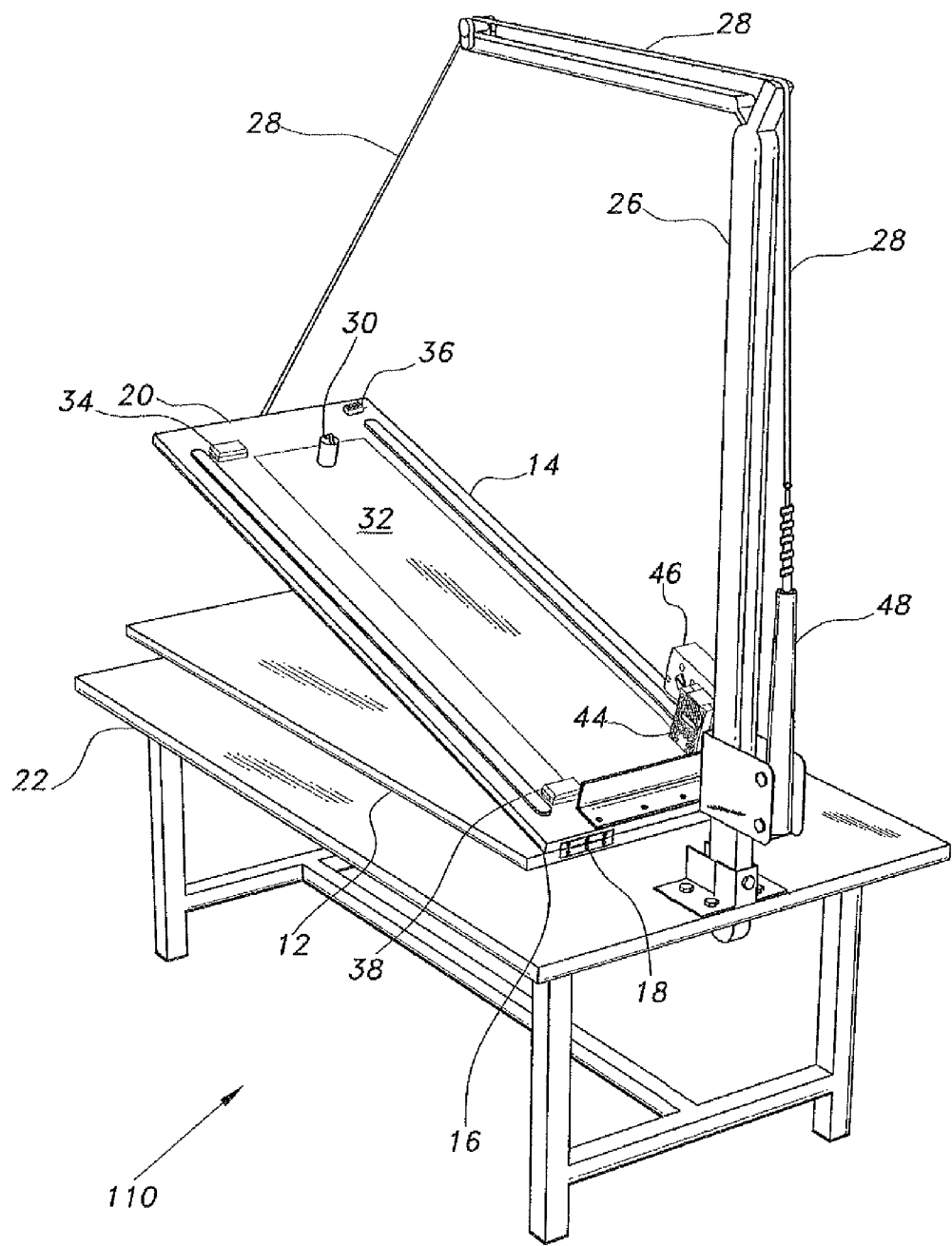
FIG. 4 is a perspective view of an alternative embodiment of an apparatus for determining coefficients of friction according to the present invention that has a jackscrew for the adjustment of the angular elevation of the ramp.

FIG. 4 of the drawings illustrates an alternative embodiment 110 of the apparatus for determining coefficients of friction. Most of the apparatus 110 is identical to the apparatus 10 of FIGS. 1 and 2, with the exception of the means used to raise and lower the elevating end 20 of the ramp 14. Rather than using a manually actuated ratchet winch, the apparatus 110 of FIG. 4 uses a jackscrew assembly 48 mounted to the lower end of the column 26. The cable 28 is connected to the extendible and retractable element of the jackscrew assembly 48, and extends up the column 26, along the arm of the column, and down to the elevating end 20 of the ramp 14 to raise and lower that end of the ramp accordingly. The provision of a jackscrew assembly 48 provides much greater smoothness of operation in comparison to the manually operated ratchet winch 24 of the apparatus 10 of FIGS. 1 through 3, thus providing greater accuracy in measurement due to the elimination of vibration during adjustment of the slope of the ramp 14.

Figure 5:
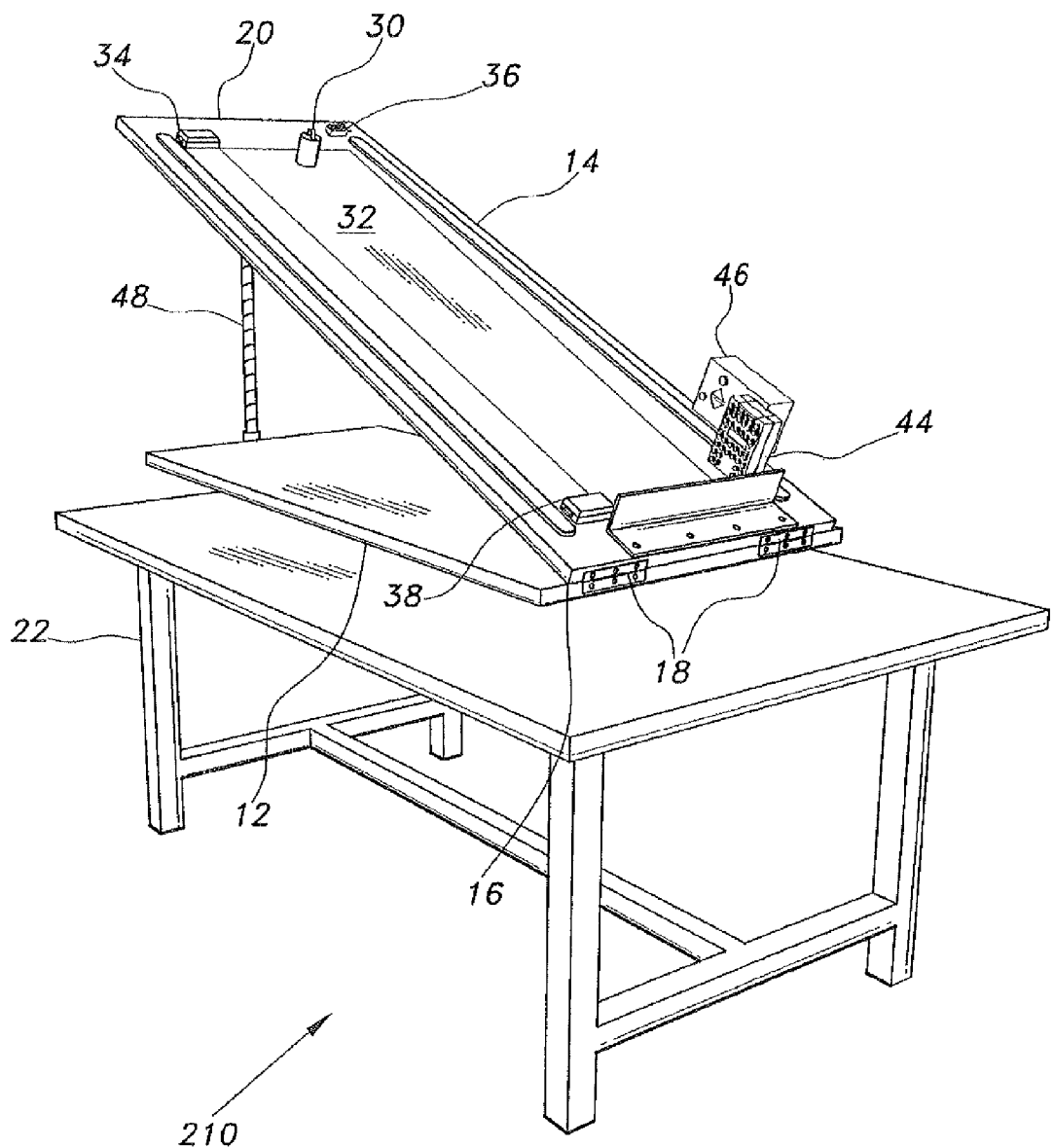
FIG. 5 is a perspective view of another alternative embodiment of an apparatus for determining coefficients of friction according to the present invention, having a jackscrew at the opposite end of the ramp from the configuration of FIG. 4.

FIG. 5 of the drawings is an illustration of a further alternative embodiment, designated as apparatus 210 for determining coefficients of friction. The apparatus 210 is similar to the other apparatus 10 and 110, but the jackscrew assembly 48 is mounted to the base 12 at the elevating end 20 of the ramp 14. The retracting and extending element of the jackscrew assembly 48 is attached to the elevating end 20 of the ramp 14 to raise and lower that end 20 of the ramp 14 directly, rather than requiring a column and cable. The same advantage of smoothness of operation provided by the apparatus 110 of FIG. 4 is provided in the apparatus 210.

Accordingly, the precision provided by apparatus 10, 110, and 210 for determining coefficients of friction, particularly the jackscrew apparatus 110 and 210 of FIGS. 4 and 5, greatly facilitates the precise measurement and determination of the coefficients of friction between different materials. The increased accuracy of the resulting measurements may be applied to many different technical fields to advance the materials and technology in those fields.

In use, the operator selects a mass 30-30e and a surface 32-32b of the types of material to be tested. The ramp 14 is gradually raised by the winch 24 or the jackscrew 48. The instantaneous slope angle (the angle between the ramp 14 and the base 12) is displayed on the digital angle meter 44. The coefficient of static friction may be determined by the equation:

$$\mu s = \tan \phi$$

where μs is the coefficient of static friction and ϕ is the slope angle of the ramp at which the mass first starts to slide. The operator may perform the calculation using manually using trigonometric tables, by using an electronic hand calculator having trigonometric functions, or in any other manner.

In order to determine the coefficient of kinetic friction, the operator applies power to the lights 34, 38, sensors 36, 40, digital angle meter 44, and timing device 46. The operator selects a mass 30-30e and a surface 32-32b of the types of material to be tested. The ramp 14 is gradually raised by the winch 24 or the jackscrew 48. The instantaneous slope angle (the angle between the ramp 14 and the base 12) is displayed on the digital angle meter 44. The ramp 14 is raised until the mass 30-30e slides down the ramp 14 from the first sensor 36 to the second sensor 40. The elapsed time is read from the display of the timing device 46 and the slope angle is read from the digital angle meter 44. The coefficient of kinetic friction may be determined by the equation:

$$\mu k = \tan\theta - \frac{2D}{\cos(\theta)gt^2}$$

where μk is the coefficient of kinetic friction, D is the distance between the starting sensor 36 and the finish sensor 40, θ is the slope angle of the ramp 14, g is the acceleration of gravity, and t is the elapsed time. The operator may perform the calculation using manually using trigonometric tables, by using an electronic hand calculator having trigonometric functions, or in any other manner.

Thus, the apparatus provides an economical, easy to use device for determining the static and kinetic coefficients of friction for different combinations of material sliding upon different types of surfaces.

It is to be understood that the present invention is not limited to the embodiments described above, but encompasses any and all embodiments within the scope of the following claims.

I claim:

1. An apparatus for determining coefficients of friction, comprising:
    a flat, planar base;
    a ramp having a base attachment end and an elevating end opposite the base attachment end, the base attachment end being pivotally attached to the base;
    means for gradually and continuously raising the elevating end of the ramp;
    a digital angle meter having a display, the digital angle meter being mounted on the base and configured for measuring and displaying the angle between the base and the ramp;
    a plurality of test masses, the test masses each being of different materials and different masses from one another;
    a plurality of test surfaces, the test surfaces being selectively interchangeably disposed upon the ramp, wherein the plurality of test surfaces are selected from a group consisting of concrete, asphalt paving, and wood;
    a pair of timing sensors mounted on the ramp and separated by a measured distance, the timing sensors including a starting sensor mounted at the elevating end of the ramp and a finishing sensor mounted at the base attachment end of the ramp, the timing sensors having means for generating a start signal when one of the test masses slides past the starting sensor and means for generating a finish signal when one of the test masses slides past the finishing sensor; and
    a timing device connected to the timing sensors, the timing device having a display, the timing device having means for computing and displaying the elapsed time between the start signal and the finish signal.

2. The apparatus for determining coefficients of friction according to claim 1, wherein each said timing sensor comprises:
    a light source disposed upon one side of said ramp, the light source generating a beam of light; and
    a light detector disposed on a side of said ramp opposite the light source and positioned so that the beam of light is incident upon the detector.

3. The apparatus for determining coefficients of friction according to claim 2, wherein:
    said light source comprises an LED; and
    said light detector comprises a phototransistor.

4. The apparatus for determining coefficients of friction according to claim 1, wherein said means for raising comprises a mechanical winch disposed adjacent the pivotally attached end of the ramp and a cable extending from the winch to the elevating end of the ramp.

5. The apparatus for determining coefficients of friction according to claim 4, wherein the winch is a manually operated ratchet winch.

6. The apparatus for determining coefficients of friction according to claim 1, wherein said means for raising comprises a jackscrew disposed at the elevating end of the ramp.

7. The apparatus for determining coefficients of friction according to claim 1, wherein said means for raising comprises a jackscrew disposed adjacent the pivotally attached end of the ramp and a cable extending from the jackscrew to the elevating end of the ramp.

8. The apparatus for determining coefficients of friction according to claim 1, wherein each said test mass is cylindrical.

* * * * *